United States Patent
Deshpande et al.

(10) Patent No.: US 6,713,625 B2
(45) Date of Patent: Mar. 30, 2004

(54) PROCESS FOR THE PREPARATION OF CEFDITOREN USING THE THIOESTER OF THIAZOLYLACETIC ACID

(75) Inventors: Pandurang Balwant Deshpande, Tamilnadu (IN); Parven Kumar Luthra, Tamilnadu (IN)

(73) Assignee: Orchid Chemicals & Pharmaceuticals Ltd., Tamil Nadu (IN)

( * ) Notice: Subject to any disclaimer, the term of this patent is extended or adjusted under 35 U.S.C. 154(b) by 0 days.

(21) Appl. No.: 10/152,791

(22) Filed: May 23, 2002

(65) Prior Publication Data

US 2003/0225265 A1 Dec. 4, 2003

(51) Int. Cl.⁷ .............................................. C07D 501/24

(52) U.S. Cl. ..................................................... 540/227

(58) Field of Search ........................................ 540/227

(56) References Cited

U.S. PATENT DOCUMENTS

| | | | | |
|---|---|---|---|---|
| 5,869,649 A | * | 2/1999 | Khanna et al. | 540/227 |
| 6,388,070 B1 | * | 5/2002 | Deshpande et al. | 540/227 |
| 6,555,680 B1 | * | 4/2003 | Deshpande et al. | 540/227 |

* cited by examiner

Primary Examiner—Mark L. Berch
(74) Attorney, Agent, or Firm—Burns, Doane, Swecker & Mathis, L.L.P.

(57) ABSTRACT

The present invention provides a process for the preparation of Cefditoren of the formula (I)

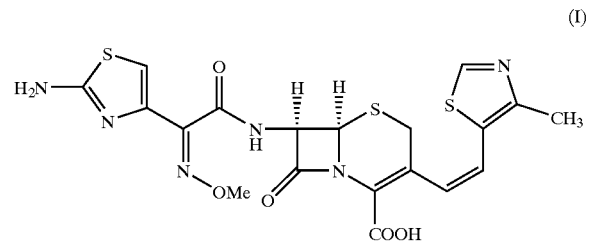

which comprises acylating 7-amino-cephem carboxylic acids of the general formula (IV)

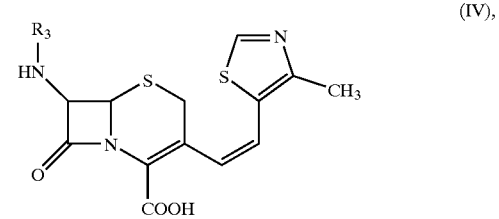

where $R_3$ is hydrogen or trimethylsilyl with thioester derivatives of the formula (II)

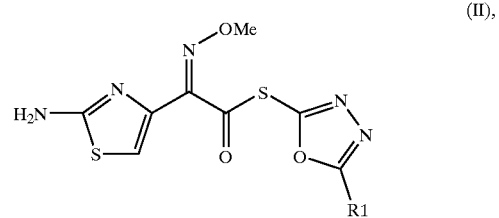

wherein $R_1$ represents $C_1$–$C_4$ alkyl or phenyl in an organic solvent in the presence of an organic base at a temperature in the range of –10° C. to 30° C.

10 Claims, No Drawings

PROCESS FOR THE PREPARATION OF CEFDITOREN USING THE THIOESTER OF THIAZOLYLACETIC ACID

FIELD OF INVENTION

The present invention relates to a process for the preparation of Cefditoren of formula (I), the pivaloyloxy methyl ester (Cefditoren pivoxil) of which is well known to be used as an antibiotic agent.

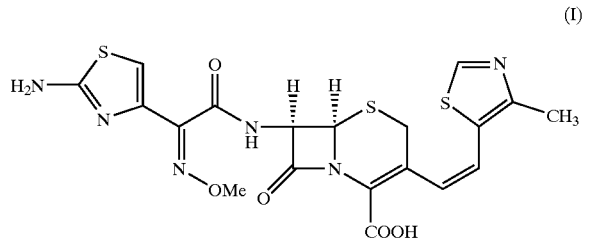

The present invention more particularly relates to a process for the preparation of Cefditoren using the thioester derivatives of formula (II)

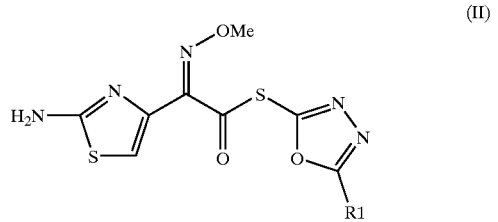

wherein, $R_1$ represents $C_1-C_4$ alkyl or phenyl. The thioester derivatives of formula (II) have been disclosed and claimed in the U.S. Pat. No. 6,388,070.

BACKGROUND OF THE INVENTION

Acid chlorides, anhydrides, esters, amide etc. are reported in the chemical literature for activation of carboxylic acid of formula (III).

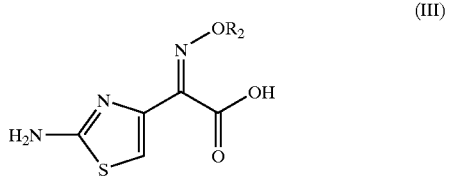

wherein, $R_2$ represents H, trityl, $CH_3$, $CR_aR_bCOOR_c$, (in which $R_a$ and $R_b$ independently of one another represent hydrogen or methyl and $R_c$ represents H or $C_1-C_7$ alkyl).

In these, activation in the form of acid chloride required protection and deprotection of $NH_2$ group.

Activation of acid (III) is reported by $SO_2Cl_2/DMF$ in U.S. Pat. No. 5,856,502 and $SOCl_2/DMF$ in U.S. Pat. No. 5,037,988. These processes suffer the limitation of using harmful and pungent smelling chemicals like $SOCl_2$, $SO_2Cl_2$ along with solvents like benzene, toluene, etc. and stringent conditions required for carrying out the reactions at commercial scale.

In U.S. Pat. Nos. 4,576,749 and 4,548,748 the acid of formula (III) has also been activated by reacting with 1-hydroxybenzotriazole (HOBT) or 2-mercaptobenzothiazole (MBT) in the presence of dicyclohexylcarbodiimide (DCC) to produce reactive ester of the acid (III) which then reacted to cephem moiety to prepare cephem antibiotics, but the processes are time consuming and with low yields, hence not suitable.

U.S. Pat. No. 4,767,852 discloses a process for the production of cephems by acylating 7-amino-3-cephem-4-carboxylic acid with 2-mercaptobenzothiazolyl-(Z)-2-(2-aminothiazol-4-yl)-2-methoxyiminoacetate (MAEM). Similarly, U.S. Pat. No. 5,026,843 (1991) discloses a process for preparing ceftriaxone disodium hemiheptahydrate by acylation of ACT by using MAEM as acylating agents in good yield and quality. Thus, MAEM has become the standard acylating agent for the preparation of cephalosporins having an oximino group and a 2-aminothiazolyl group in 7-position of cephem compounds.

However, the synthesis of MAEM from acid (III) and 2,2'-dithio-bis-benzothiazole involves use of costly condensing agent triphenylphosphine (TPP). Moreover, during condensation of MAEM with 7-amino-3-cephem-4-carboxylic acid compound (IV), a toxic compound MBT is also produced as a byproduct, see e.g., Chemical Abstracts, 111, 19243$_P$ (1989) which is difficult to remove completely.

Thus, it is evident that the procedures described in the prior art for preparation of these antibiotics are complex, involving protection, deprotection and are associated with toxic byproduct generation. Hence, there is a need to develop new acylating agents which are capable of transferring the 2-aminothiazolyl moiety to cephem compounds of formula (IV) in good yield but without producing this toxic byproduct. On the similar lines, a new thioester was reported by D. G. Walker, Tet. Lett. 1990, 31,6481 to acylate the cephem moiety to get cefepime sulfate but yields obtained by using this thioester were in the range of 54–73% which cannot be considered as good yield to operate the process at commercial scale. The use of this thioester was also reported in the Tet. Lett. 1990, 31, 6481 only for cefepime and not for other cephalosporins. This thioester was exploited in U.S. Pat. No. 5,869,649 for making three other important cephalosporin antibiotics.

OBJECTIVES OF THE INVENTION

The primary objective of the invention is to provide a process for the preparation of Cefditoren of formula (I), using the thioester derivatives of thiazolyl acetic acid of the general formula (II), which is a better reactive derivative than the other reactive derivatives.

Another objective of the present invention is to provide a process for the preparation of Cefditoren of formula (I), which is simple, high yielding and cost effective.

Still another objective of the present invention is to produce Cefditoren of formula (I), which is highly pure and free from toxic by-products.

SUMMARY OF THE INVENTION

Accordingly, the present invention provides a process for the preparation of Cefditoren of formula (I), which comprises acylating 7-amino-cephem carboxylic acid of the general formula (IV) where $R_3$ is hydrogen or trimethylsilyl group with thioester derivative of formula (II) where $R_1$ represents $C_1$–$C_4$ alkyl or phenyl in an organic solvent and in the presence of an organic base at a temperature in the range of −10° C. to 30° C.

The process is shown in Scheme-1 herebelow:

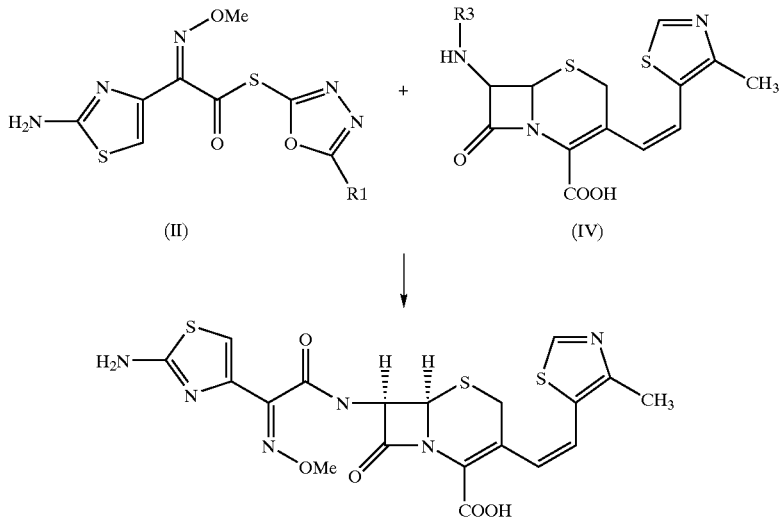

Scheme-1

Wherein, $R_1$ and $R_3$ are as defined above.

DETAILED DESCRIPTION OF THE INVENTION

The condensation of cephem compound of formula (IV) with thioester of formula (II) is performed by two different methodologies (a) by acylating the compound of formula (IV) (when $R_3$ is H) with formula (II) in an aqueous organic solvent; (b) by acylating the compound of formula (IV) (when $R_3$ is silyl) with formula (II) in an aprotic organic solvent. Both the approaches are comparable and afforded excellent yields and purities of cephalosporin antibiotics of formula (I).

Acylation of compounds of formula (IV) (when $R_3$ is H) is performed in the presence of a water miscible solvent selected from tetrahydrofuran (THF), acetonitrile, acetone, dioxane, N,N-dimethylformamide etc., but the preferable solvent is THF or acetonitrile.

Acylation of compound of formula (IV) (when $R_3$ is silyl) was carried out in an aprotic organic solvent selected from halogenated hydrocarbons, toluene, alkyl ethers etc., but preferable solvent is dichloromethane. Suitable silylating agent used for the reaction is selected from hexamethyldisalazane, bis(trimethyl)silylacetamide or trimethylsilyl chloride.

In another embodiment of the present invention, the organic base may be selected from triethylamine, diethylamine, tributylamine, N-alkylpyridine, N-alkylanilines, 1,8-diazabicyclo[5.4.2]undec-7-ene, 1,5-diazabicyclo[4.3.0]non-5-ene, N-methylmorpholine, 1,4-diazabicyclo[2.2.2]octane, 4-dimethylamino pyridine or mixtures thereof.

In another embodiment of the present invention, the Cefditoren of formula (I) obtained is a syn-isomer.

In yet another embodiment of the present invention, the Cefditoren of the formula is Z-isomer.

The present invention provides a method by which cephalosporin antibiotics are obtained in high purity (95–99%) and excellent yield (79–95%) without the necessity for protecting the amino group of the acylating agents and the production of toxic byproduct namely 2-mercaptobenzothiazole is avoided.

Many other beneficial results can be obtained by applying disclosed invention in a different manner or by modifying the invention with the scope of disclosure. However, since the major characteristic feature of the present invention resides in the use of novel reactive thioester derivatives of thiazolyl acetic acid of the general formula (II) in preparing the Cefditoren of formula (I) the technical scope of the present invention should not be limited to the following examples.

The following examples are provided to illustrate but not to limit the claimed invention.

EXAMPLES

Example-I

Synthesis of 2-Mercapto-5-phenyl-1,3,4-oxadiazolyl-(Z)-2-(2-aminothiazol-4-yl)-2-methoxyimino Acetate (II):

(Z)-(2-aminothiazol-4-yl)methoxyimino acetic acid (20.1 g), triethylamine (22.2 g) were suspended in dry dichloromethane (150 ml), and then bis-(2-oxo-oxazolidinyl) phosphinic chloride (25.4 g) was added in one lot at 0–5° C. and stirred for 1 hr. The 2-mercapto-5-phenyl-1,3,4-oxadiazole (21.3 g) was added at 0–5° C. The reaction mixture was stirred for 3–4 hours. After the reaction was complete, distilled water (100 ml) was added to the reaction solution and the mixture was stirred for 10 min. The organic layer was separated and washed successively with 2% aq. solution bicarbonate solution (100×2 ml) and saturated saline (100 ml), dried over sodium sulphate, filtered and then concentrated under reduced pressure. To the residue, IPE (300 ml) was added and solid was filtered, washed with IPE (100 ml). Dried to obtain 30.6 g (yield 85%) of the title compound as light yellow solid.

Melting point: 109–110° C; $^1$HNMR (DMSO-$d_6$): δ 3.90 (3H ,s, N—OCH$_3$), 7.11 (1H, s, thiazole ring proton), 7.29 (2H, bs, NH$_2$), 7.6–7.9 (5H, m, —C$_6$H$_5$); $^{13}$C-NMR (Acetone-$d_6$): δ 63.16, 108.7, 122.1, 129.7, 132.6, 133.7, 141.6, 146.75, 159.3, 159.6, 169.7, 173.1.

Example-II

3-[(Z)-2-(4-Methyl-5-thiazolyl)vinyl]-7-[(Z)-(2-aminothiazolyl-4-yl)-2-(methoxyimino)acetamido]-3-cephem-4-carboxylic Acid (Cefditoren Acid):

A mixture of THF (250 ml) and water (150 ml) was stirred under inert atmosphere. At 0° C.–1° C., 7-amino-3-[(Z)-2-(methyl-5-thiazolyl)vinyl]-3-cephem-4-carboxylic acid (25.0 g) and 2-mercapto-5-phenyl-1,3,4-oxadiazolyl-(Z)-2-(2-aminothiazol-4-yl)-2-methoxyimino acetate (33.3 g) obtained in Example I were added. Triethylamine (10.5 g) was slowly added to reaction by maintaining the pH between 7.5 to 8.5. The reaction was monitored by HPLC. After 4–5 hrs., the reaction mixture was extracted by methylene chloride. The aqueous layer is subjected for charcoal (0.125 g) treatment. Ethylacetate was added to the filtrate and the solution was acidified with dil. HCl at 10° C. to pH 3.0. The solid separated was filtered, washed with water and ethylacetate and then dried under vacuum at 40–45° C. to get Cefditoren acid, 35.0 g (yield 90%).

HPLC (purity)=96–98%.

What is claimed is:

1. A process for the preparation of Cefditoren of formula (I)

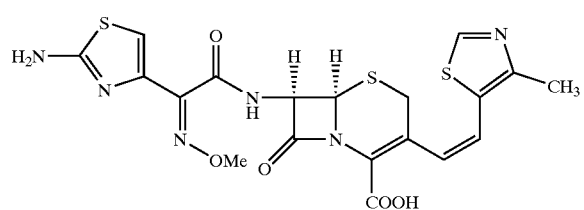

which comprises acylating a compound of formula (IV)

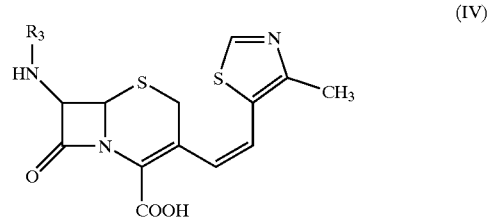

wherein, $R_3$ is hydrogen or trimethylsilyl, with a compound of formula (II)

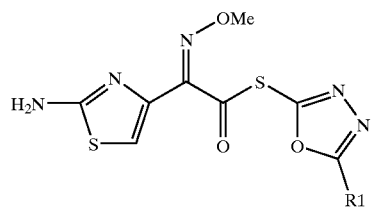

wherein $R_1$ represents $C_1$–$C_4$ alkyl or phenyl, in the presence of an organic solvent, and an organic base at a temperature in the range of –10° C. to 30° C.

2. The process of claim 1, wherein the compound of formula (I) is a syn isomer.

3. The process of claim 1, wherein $R_3$ is H, the acylation is done in the presence of a mixture of water and an organic solvent selected from the group consisting of tetrahydrofuran, acetonitrile, acetone, dioxane, N,N-dimethylformamide, and mixtures thereof.

4. The process of claim 1, wherein when $R_3$ is trimethylsilyl, the acylation is carried out in the presence of an organic solvent, an organic base and a silylating agent at a temperature in the range of –10° C. to 30° C.

5. The process of claim 1, wherein said acylation is performed in the presence of an organic base selected from the group consisting of triethylamine, diethylamine, tributylamine, N-alkylanilines, 1,8-diazabicyclo[5.4.2]undec-7-ene, 1,5-diazabicyclo[4.3.0]non-5-ene, 1,4-diazabicyclo[2.2.2]octane, 4-dimethylaminopyridine, and mixtures thereof.

6. The process of claim 4, wherein the silylating agent used is trimethylsilyl halide.

7. The process of claim 6, wherein the trimethylsilyl halide used is trimethylsilyl chloride.

8. The process of claim 4, wherein the organic solvent is selected from the group consisting of halogenated hydrocarbon, toluene and an alkyl ether.

9. The process of claim 8, wherein the organic solvent is an alkyl ether.

10. The process of claim 4, wherein said acylation is performed in the presence of an organic base selected from the group consisting of triethylamine, diethylamine, tributylamine, N-alkylanilines, 1,8-diazabicyclo[5.4.2]undec-7-ene, 1,5-diazabicyclo[4.3.0]non-5-ene, 1,4-diazabicyclo[2.2.2]octane, 4-dimethylaminopyridine, and mixtures thereof.

* * * * *